(12) United States Patent
Pausch et al.

(10) Patent No.: US 6,482,183 B1
(45) Date of Patent: Nov. 19, 2002

(54) APPARATUS FOR THE FIXATION OF A PERCUTANEOUS FLEXIBLE LINE

(76) Inventors: Gudrun Pausch, Pfieffrain 56, D-34212 Melsungen (DE); Ralf Jaeckel, Schiessstattstrasse 1, D-83024 Rosenheim (DE)

(*) Notice: Subject to any disclaimer, the term of this patent is extended or adjusted under 35 U.S.C. 154(b) by 0 days.

(21) Appl. No.: 09/567,601

(22) Filed: May 10, 2000

(51) Int. Cl.$^7$ .............................................. A61M 5/32
(52) U.S. Cl. ....................................... 604/174; 604/910
(58) Field of Search ................................. 604/174, 175, 604/177, 178, 910

(56) References Cited

U.S. PATENT DOCUMENTS 4,645,492 A * 2/1987 Weeks ........................ 604/174
5,267,969 A * 12/1993 Hirsch et al. ................ 604/174
5,690,616 A * 11/1997 Mogg .......................... 604/174
6,231,547 B1 * 5/2001 O'Hara ........................ 604/174

* cited by examiner

*Primary Examiner*—Edward K. Look
*Assistant Examiner*—Michael Leslie
(74) *Attorney, Agent, or Firm*—William B Ritchie

(57) ABSTRACT

A fixation mechanism used for attaching a flexible line or any other catheter extending through the abdominal wall or percutaneously applied in any other location during a percutaneous endoscopic gastrostomy (PEG). The fixation mechanism utilizes a cover plate fitted with a support base through which the flexible line (10) is placed. In order to attach the flexible line, a barrel vault-shaped body is folded and clicked into a closed position. The flexible line extending outside the abdominal wall (14) is then folded at an angle of 90° without appreciably changing its cross-sectional pre-insertion dimensions.

6 Claims, 2 Drawing Sheets

APPARATUS FOR THE FIXATION OF A PERCUTANEOUS FLEXIBLE LINE

This application claims priority under 35 U.S.C. §365(c) based on the PCT Application No. PCT/DE98/03285, filed Nov. 10, 1998 and having a priority date of Nov. 11, 1997 based on German Patent Application No. 197 49 741.1.

FIELD OF THE INVENTION

This invention relates to the field of percutaneous endoscopic gastrostomy (PEG) and, in particular, attaching a percutaneously applied flexible line or tube to the skin.

BACKGROUND OF THE INVENTION

The problem of fixating a PEG tube or line in position on a patient's skin is well known in the art. A typical solution is disclosed in WO 94/08648. This device is primarily used during a percutaneous endoscopic gastrostomy (PEG) and serves as fixation device for a percutaneous catheter. During a percutaneous endoscopic gastrostomy, as described in DE 9112338U1, a cannula is inserted into the stomach through a hole that is placed in the abdominal wall. A suture is then thread through the cannula. Using an endoscope, the end of the suture is grasped and guided up through the patient's mouth. The suture is then attached to the flexible line or tube and the tube is guided down through the esophagus into the stomach and out through the abdominal incision where the flexible line leaves percutaneously. One end of the line is attached to the inner abdominal wall of the stomach. The flexible line or cannula serves for example as catheter for enteral feeding.

To avoid unintentional movement, a fixation device is required at the outside of the abdominal wall. A typical fixation device is disclosed in WO 94/08648 comprising a covering plate with a hole for the flexible line that is attached to the patient's abdominal wall. On top of the cover plate, there is a supporting plate with an open channel on its edge having in its cross section the shape of a semicircle. In the first area, the channel runs vertically to the cover plate, and after bending in the second area, it runs parallel to the cover plate. The result achieved is that the flexible line leaves the patient's body vertically but is then rerouted parallel to the skin surface. The cover plate in both mentioned areas has solidly affixed mechanisms that close the channel's aperture and constitute eyelets through which the flexible line has to pass.

However, one difficulty in using the above-mentioned fixation device as well as other prior art devices is that during the process of inserting the flexible line into the fixation device, the flexible line changes diameter. A fixation device that does not cause the diameter of the flexible to appreciably change, provides a simple insertion of the flexible line and an easy way to move it to for adaptation to the individual situation, can operated single handedly, and enables the fixation of the flexible line in a 90° angle without the flexible line becoming crimped or bent is not found in the prior art.

SUMMARY OF THE INVENTION

The invention comprises a fixation device that presses the flexible line into a supporting wall having a channel, and a pivotally hinged securing mechanism (barrel-vault shaped body) to secure the flexible line that is flexibly attached to the cover plate. The hole for the passage of the flexible line is located between the barrel-vault shaped body's axis and the supporting wall. Therefore, the barrel-vault shaped body can be turned in the direction of the flexible line. If it is open, the flexible line passes through the cover plate directly. In closing, the barrel-vault shaped body takes hold of the flexible line and bends it onto the supporting plate's surface. With the barrel-vault shaped body open, the cover plate can be easily moved and adjusted, whereas the flexible line is fixed if the barrel-vault shaped body is closed. The fixation happens solely by using the tension in the flexible line material; consequently, its diameter remains substantively unchanged. The flexible line does not crimp or bend. This is important to guarantee an optimal and undisturbed flow of liquid through the flexible line. Another feature of the invention is the one-hand-operability of the fixation mechanism. The cover plate can easily be moved with the open barrel-vault shaped body and the fixation mechanism can be closed and locked by using only one hand.

The invention is preferably equipped with a cover plate made of soft and elastic material, while the barrel-vault shaped body is made of a stiff material. A cover plate made of soft and elastic material enables a tactile comfortable application to the patient's skin and can be used as fixation mechanism to arrest the barrel-vault shaped body at the same time.

Preferably, the barrel-vault shaped body comprises a preformed channel, that together with the channel on the supporting plate forms a cross section with the shape of a circle that covers the flexible line and keeps it in shape. This securely prevents the flexible line from being bent even if the flexible line is being pulled.

The cover plate preferably is made in a triangular shape and, at the side of the supporting wall, has triangular wings. The hole for the passage of the flexible line preferably is located close to the center of this triangle, allowing an even dispersion of pressure and avoiding local concentrated pressure. This means an optimal wearing comfort that is important because the fixation mechanism can be utilized together with a catheter for long-term enteral feeding; hence, it can be used for long periods of time. Additionally there is the possibility of plaster fixation.

Another part of the invention is a gastrostomy-set that comprises a flexible line with a retaining element and a fixation mechanism. The barrel-vault shaped body and the flexible line are attuned in a way that prevents the flexible line from being crimped or bent and keeps its tubular shape from compressing.

These aspects of the invention are not meant to be exclusive and other features, aspects, and advantages of the present invention will be readily apparent to those of ordinary skill in the art when read in conjunction with the following description, appended claims and accompanying drawings.

DETAILED DESCRIPTION OF THE INVENTION

The invention is a fixation device that allows a simple insertion of the flexible line and an easy way to move it to for adaptation to the individual situation, and on the other hand enables the fixation of the flexible line in a 90° angle without the flexible line becoming crimped or bent. The invention comprises a fixation device that presses the flexible line into a channel of a supporting wall and a pivotally hinged securing mechanism (barrel-vault shaped body) to secure the flexible line that is flexibly attached to a over plate. The hole for the passage of the flexible line is located between the barrel-vault shaped body's axis and the supporting wall. Therefore, the barrel-vault shaped body can be turned in the direction of the flexible line. If it is open, the flexible line passes through the cover plate directly. In closing, the barrel-vault shaped body takes hold of the flexible line and bends it onto the supporting plate's surface. With the barrel-vault shaped body open, the cover plate can be easily moved and adjusted, whereas the flexible line is fixed if the barrel-vault shaped body is closed. The fixation happens solely by using the tension in the flexible line material; consequently, its diameter remains unchanged. The flexible line does not crimp or bend. This is important to ensure an optimal and undisturbed flow of liquid through the flexible line.

The invention also permits one-hand-operability of the fixation mechanism. The cover plate can easily be moved with the open barrel-vault shaped body and the fixation mechanism can be closed and locked by using only one hand.

The cover plate is preferably made of soft and elastic material, while the barrel-vault shaped body is made of a stiffer material. Having the cover plate made of soft and elastic material enables a tactile comfortable application to the patient's skin and can be used as fixation mechanism to arrest the barrel-vault shaped body at the same time.

Preferably, the barrel-vault shaped body comprises a preformed channel, that together with the channel on the supporting plate forms a cross section with the shape of a circle that covers the flexible line and keeps it in shape. This securely prevents the flexible line from being bent even if the flexible line is being pulled.

The cover plate preferably is made in a triangular shape and, at the side of the supporting wall, has triangular wings. The hole for the passage of the flexible line preferably is located close to the center of this triangle, allowing an even dispersion of pressure, comprising a cover plate with a hole for the flexible line, whereas the plate folds the flexible line at an angle of 90°.

Figure 1:
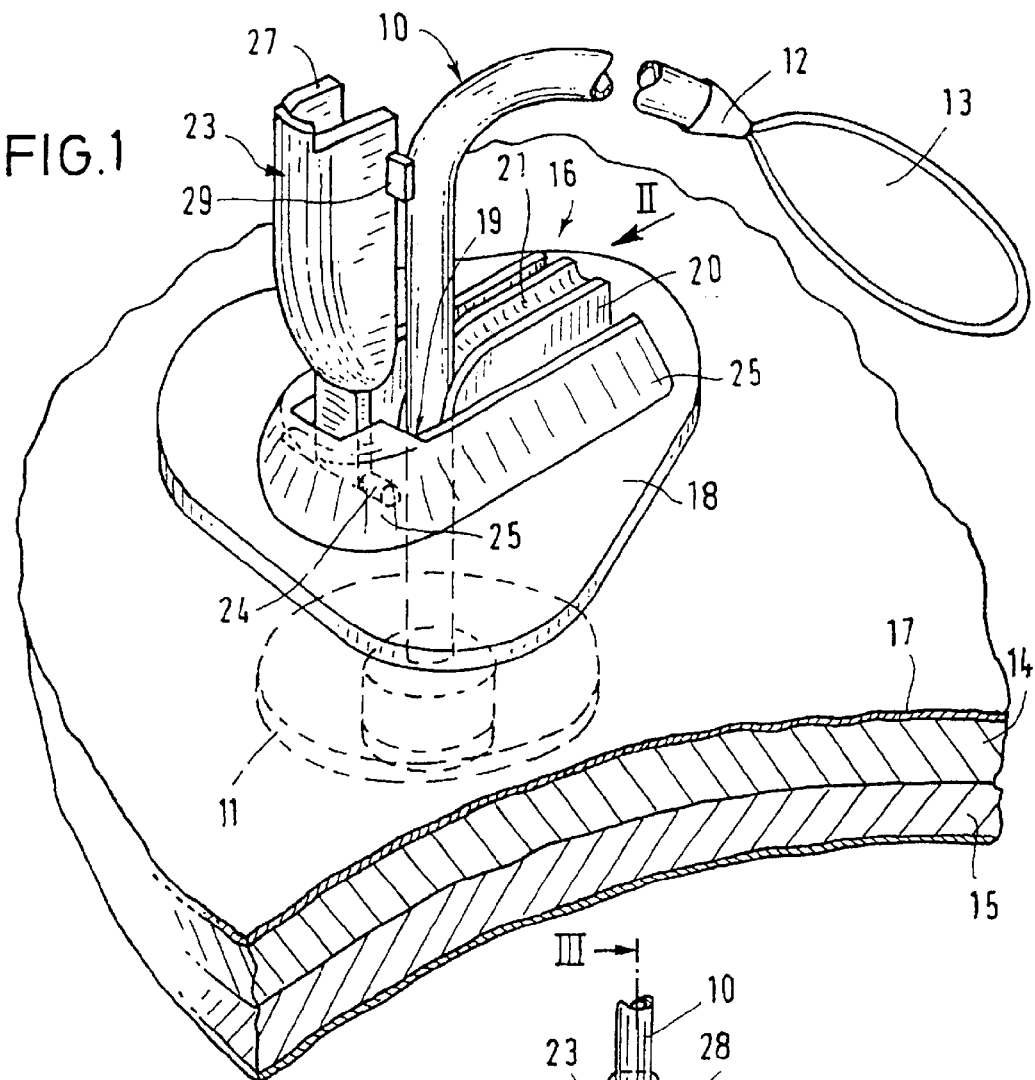
FIG. 1 is a perspective view of the fixation mechanism in accordance with the invention before its fixation to a flexible line that percutaneously enters the abdominal wall.
Figure 2:
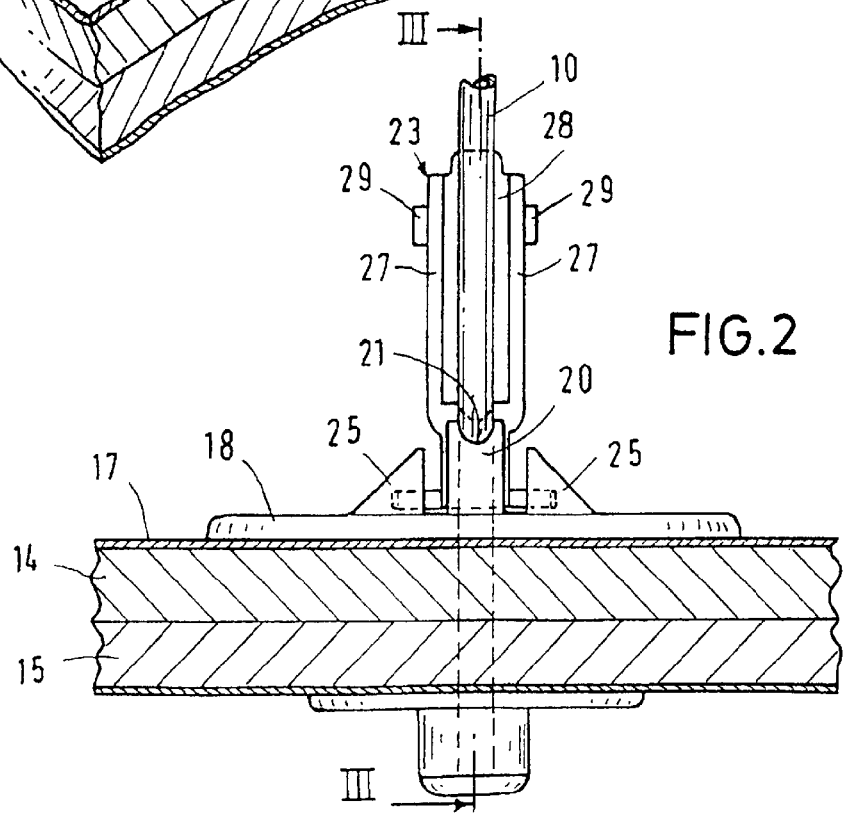
FIG. 2 is a cross-sectional view of the fixation mechanism in the direction of the arrow 11 as shown in FIG. 1.

As shown in FIG. 1, flexible line 10 is used as enteral catheter. The flexible line 10 has a retaining element 11 at its end with the shape of a dish and a sling 13 at its sling attachment end 12. The flexible line 10 is inserted into the stomach through the esophagus with its sling attachment end 12 first. It exits distally through the previously punctured abdominal wall 14 and the inner side stomach wall 15 with the help of a suture attached to the sling 13. Then, the sling attachment end 12 of the flexible line 10 can be pulled out of the patient's body with the retaining element 11 remaining at the inner side stomach wall 15. The flexible line 10 is fixed by fixation mechanism 16, which is applied from the outside to the patient's skin.

The fixation mechanism 16 comprises cover plate 18 that essentially has the shape of a triangle with three equal sides and with rounded corners. In the cover plate 18, there is aperture 19 to allow the flexible line 10 to pass through. The sling attachment end 12 of the flexible line 10 is put through this aperture 19 and the cover plate 18 is threaded onto and moved along the flexible line 10 until its underside rests upon the skin 17.

Figure 3:
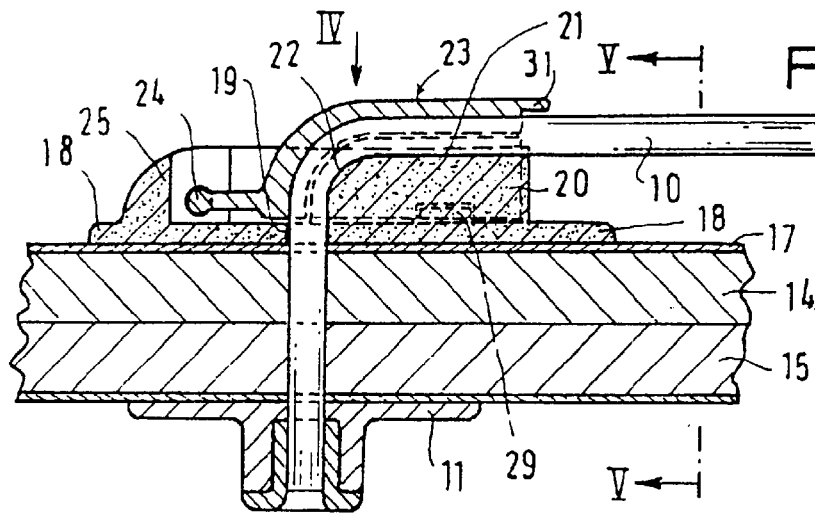
FIG. 3 is a cross-sectional view along line III—III of FIG. 2 with the fixation mechanism closed.

The cover plate 18 has a support base 20 vertically attached with a support channel 21 on top of it. This support channel 21 has a cross-section of a semicircle and is dimensioned to accommodate approximately one-half the diameter surface of flexible line 10. The support channel 21 runs, as shown in FIG. 3, in the shape of the bow 22 to the aperture 19. The flexible line 10 is being bent in the bow 22 in a 90° angle at the support base 20 and runs in the support channel 21 parallel to the cover plate 18.

Figure 5:
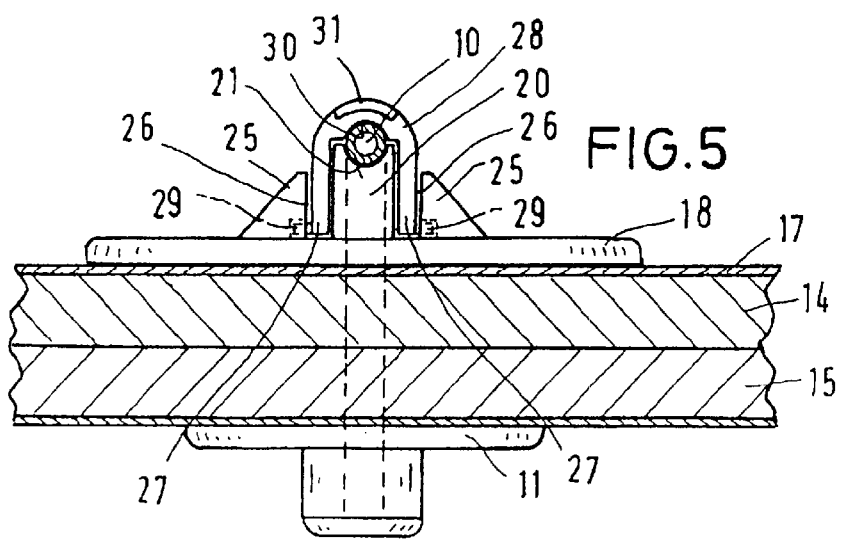
FIG. 5 is a cross-sectional view on the fixation mechanism in direction of arrows V—V of FIG. 3.

At the cover plate 18, barrel vault-shaped body 23 is installed, which is attached to the pivotal axis 24. The aperture 19 is located between the pivotal axis 24 and the support base 20. The pivotal axis 24 is attached to the barrel vault-shaped body 23 and anchored in the side parts 25 of the cover plate 18. The side parts 25 are elevated at the side of the support base 20. Between the support base 20 and the side parts 25, there are locking grooves 26. (see FIG. 5).

The barrel vault-shaped body 23 has the shape of a stretched shovel with two parallel side flanks 27 and a vault-shaped middle part 28 connecting the side flanks 27. There are locking element 29 connected to the side flanks 27 that lock into the side parts 25 if the barrel vault-shaped body 23 is put in its locking position according to FIG. 3. The barrel vault-shaped body 23 comprises a channel 30 (see FIG. 5) in the shape of a semicircle, which is embedded into the support base 20 of the support channel 21 which closes over the flexible line 10 forming a tunnel around the flexible line 10. This channel 30 goes through the bending area of the barrel vault-shaped body 23 opposite of the bow 22, so that the barrel vault-shaped body 23 entirely holds and forms the flexible line 10. The flexible line's 10 diameter, which is formed by the support channel's 21 and channel's 30 profile, corresponds to the outer diameter of the flexible line 10, so that it can hold the flexible line 10. The flexible line 10 is fixated by means of the 90° angle and the friction of the line 10 against the supporting tunnel.

The closed barrel vault-shaped body 23 can be flipped to the open position by grabbing the handle 31 (see FIG. 5) at the end of the barrel vault-shaped body 23. By applying force to open the barrel vault-shaped body 23, the locking element 29 is pushed out of its resting location. The barrel vault-shaped body 23 can be put into its locking position at the cover plate 18 by merely pressing it down. The cover plate 18 is preferably made of soft and elastic material, while the barrel vault shaped body 23 preferably is made of hard or less elastic plastic.

Figure 4:
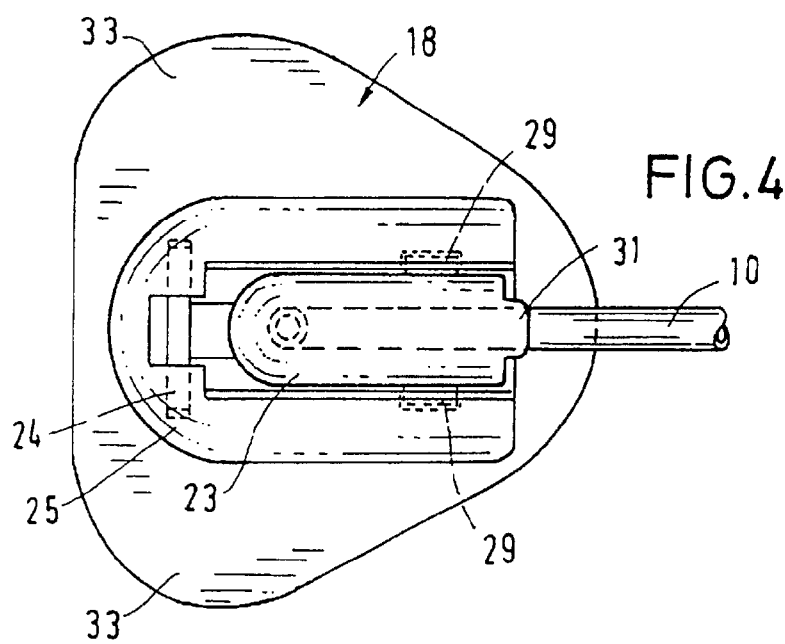
FIG. 4 is a top view of the fixation mechanism.

As FIG. 4 shows, the cover plate 18 has the basic shape of a triangle. At both sides of the barrel vault-shaped body 23, there are triangular wings 33. At the triangular wings 33, the cover plate 18 is very thin and highly flexible. These triangular wings 33 can be affixed with bandages to the patient's skin. The triangular wings 33 do not have sharp edges and thereby achieve equal distribution of pressure on the patient's skin without the danger of punctual imprints on the patient's skin. The aperture 19 is located adjacent to the center point of the cover plate 18 and aligned with support base 20 and pivotal axis 24.

After the flexible line 10 is set up as shown in FIG. 1, the fixation mechanism 16 is mounted on the flexible line 10 and attached to the skin 17. By moving the fixation mechanism 16 on the flexible line 10, the appropriate distance of the fixation mechanism 16 from the retaining element 11 can be determined. To simplify this, there are metering marks on the flexible line 10 (not shown). Next, the barrel vault-shaped body 23 is pressed down and locked with the locking element 29. Finally, the locking element 29 and the triangular wings 33 of the cover plate 18 are attached with bandages to the patient's body. If necessary, the barrel vault-shaped body 23 can be reopened to service and/or readjust the fixation mechanism 16 and/or administer to the patient.

Although the present invention has been described in considerable detail with reference to certain preferred versions thereof, other versions would be readily apparent to those of ordinary skill in the art. Therefore, the spirit and scope of the appended claims should not be limited to the description of the preferred versions contained herein.

What is claimed is:

1. An apparatus for the fixation of a percutaneous flexible line having a diameter to a patient, said apparatus comprising:
    a cover plate having an aperture to allow the flexible line to pass through, said cover plate comprising as soft, flexible material;
    an attached support base that comprises a support channel which holds a part of the flexible line's diameter and bends the flexible line approximately parallel to the cover plate;
    a barrel vault-shaped body having side flanks, and wherein said barrel vault-shaped body is for holding the flexible line down, said barrel vault-shaped body comprising a material that is substantially less flexible that the material of said cover plate, wherein the barrel vault-shaped body pivots around a pivotal axis at a substantially right angle to the support base, and wherein the aperture is located between the pivotal axis of the barrel vault-shaped body and the support base.

2. The apparatus of claim 1 wherein the barrel vault-shaped body combined with the support channel and the support base comprise a tubular-shaped channel.

3. The apparatus of claim 1, wherein the barrel vault-shaped body further comprises a locking element such when in a locked state, the locking element of the barrel vault-shaped body is fastened to the cover plate.

4. The apparatus of claim 1 wherein the support base further comprises a pair of locking grooves that helps fasten the side flanks of the barrel vault-shaped body to the support base.

5. The apparatus of claim 1 wherein the cover plate is essentially triangular shaped with triangular wings at the sides of the support.

6. A gastrostomy set for percutaneous endoscopic-controlled gastrostomy including a tube having a retaining element and a fixation apparatus for the fixation of the percutaneous placed tube at the skin, said set comprising:
    a cover plate having an aperture to allow the tube to pass through and a support wall following thereto having a groove which receives a part of the circumference of said tube and bends the tube approximately parallel to the cover plate, and a holding-down device holding the tube in the groove,
    wherein the holding-down device is formed by a swing clamp which is pivotable about an axis extending in a traverse direction in respect to the support wall and wherein the aperture is disposed between the axis of the swing clamp and the support wall,
    wherein the swing clamp and the tube are adjusted to each other such that the cross section of the tube will not be changed when the swing clamp is in its closed position.

* * * * *